§§

US009217042B2

(12) United States Patent
Consigny

(10) Patent No.: US 9,217,042 B2
(45) Date of Patent: Dec. 22, 2015

(54) METHOD OF REDUCING MACE IN DIABETIC PATIENTS SUBSEQUENT TO STENT PLACEMENT

(71) Applicant: Abbott Cardiovascular Systems Inc., Santa Clara, CA (US)

(72) Inventor: Paul M. Consigny, San Jose, CA (US)

(73) Assignee: ABBOTT CARDIOVASCULAR SYSTEMS INC., Santa Clara, CA (US)

(*) Notice: Subject to any disclaimer, the term of this patent is extended or adjusted under 35 U.S.C. 154(b) by 524 days.

(21) Appl. No.: 13/658,699

(22) Filed: Oct. 23, 2012

(65) Prior Publication Data

US 2014/0114401 A1    Apr. 24, 2014

(51) Int. Cl.
*A61F 2/06* (2013.01)
*C07K 16/46* (2006.01)
*A61L 27/50* (2006.01)
*A61K 39/00* (2006.01)

(52) U.S. Cl.
CPC ......... *C07K 16/468* (2013.01); *A61K 2039/505* (2013.01); *A61K 2039/54* (2013.01); *A61L 27/507* (2013.01)

(58) Field of Classification Search
CPC ........... A61F 2/06; A61F 2/82; A61L 27/507; A61M 31/00
USPC ............................ 623/1.41–1.48; 423/133.1
See application file for complete search history.

(56) References Cited

U.S. PATENT DOCUMENTS

| 7,612,181 | B2 * | 11/2009 | Wu et al. | 530/387.3 |
| 8,258,268 | B2 | 9/2012 | Wu et al. | |
| 8,586,714 | B2 * | 11/2013 | Ghayur et al. | 530/387.3 |
| 8,779,101 | B2 * | 7/2014 | Hsieh et al. | 530/387.1 |
| 2009/0311253 | A1 * | 12/2009 | Ghayur et al. | 424/133.1 |
| 2011/0137406 | A1 * | 6/2011 | Carpenter et al. | 623/1.42 |
| 2011/0264190 | A1 * | 10/2011 | McClain et al. | 623/1.11 |
| 2013/0171059 | A1 * | 7/2013 | Ghayur et al. | 424/1.11 |
| 2013/0344073 | A1 * | 12/2013 | Schwaeble et al. | 424/136.1 |
| 2014/0161804 | A1 * | 6/2014 | Cuff et al. | 424/136.1 |
| 2014/0213771 | A1 * | 7/2014 | Ghayur et al. | 530/387.3 |

FOREIGN PATENT DOCUMENTS

| WO | WO 2007/024649 | 3/2007 |
| WO | WO 2007/136516 | 11/2007 |
| WO | WO 2012/061558 | 5/2012 |

OTHER PUBLICATIONS

International Search Report and Written Opinion for PCT/US2013/064369, mailed Apr. 9, 2014, 17 pgs.

Aoki et al., "Endothelial Progenitor Cell Capture by Stents Coated with Antibody Against CD34", J. of the American College of Cardiology, vol. 45, No. 10, pp. 1574-1579 (2005).
Charnock et al., "Retention of Leukocytes in the Diabetic Wound Environment", Endocrine Abstracts 28 p. 206 (2012) 1 pg.
Frazier et al., "Inflammatory Protein Levels and Depression Screening After Coronary Stenting Predict Major Adverse Coronary Events", Sage Journals, downloaded from: www.brn.sagepub.com/content/early/2009/02/26/1099800409332801.short, Jun. 27, 2012, Abstract 1 pg.
Hashimoto et al., "Activation of endothelial nitric oxide synthase by cilostazol via a cAMP/protein kinase A-and phosphatidylinositol 3-kinase/Akt-dependent mechanism", Atherosclerosis 189, pp. 350-357 (2006).
Inflammation, Cytokines & Cells Encyclopedia-COPE, downloaded from: www.copewithcytokines.de/cope.cgi?key=inflammation, Jun. 27, 2012, 2 pgs.
Lee et al., "Drug-Eluting Stenting Followed by Cilostazol Treatment Reduces Late Restenosis in Patients with Diabetes Mellitus", J. of Am. College of Cardiology vol. 51, No. 12, pp. 1181-1187 (2008).
Miller et al., "Recent developments in nitric oxide donor drugs", Br. J. Pharmacol. 151 (3) pp. 305-321 (2007).
Murray et al., "Proinflammatory Cytokines", Circulation 107, pp. 1460-1462 (2003).
Ogbru et al., "Citazol, Pletal", MedicineNet.com, downloaded from: www.medicinenet.com/cilostazol/article.htm, Jun. 19, 2012 , 4 pgs.
Ota et al., "Cilostazol Inhibits Oxidative Stress-Induced Premature Senescence Via Upregulation of Sirt1 in Human Endothelial Cells", Arterioscler. Thromb. Vasc. Biol. 28, pp. 1634-1639 (2008).
Ota et al., "Sirolimus and Everolimus Induce Endothelial Cellular Senescence Via Sirtuin1 Down-Regulation", J. of Am. College of Cardiology vol. 53, No. 24, pp. 2298-2305 (2009).
Potente et al., "A Novel Signaling Network in Endothelial Senescence", Arterioscler. Thromb. Vasc. Biol. 28, pp. 1577-1579 (2008).
Sahelian "Cytokines and inflammation and how they influence depression and various medical diseases", downloaded from: www.ray.sahelian.com/cytokines.html, Jun. 27, 2012, 4 pgs.
Wu et al., "Molecular construction and optimization of anti-human IL-1α/β dual variable domain immunoglobulin (DVD-Ig TM) molecules", mAbs vol. 1, Issue 4, pp. 339-347 (2009).
Yamamoto et al., "Locally Applied Cilostazol Suppresses Neointimal Hyperplasia and Medial Thickening in a Vein Graft Model", Ann. Thorac Cardiovasc. Surg. vol. 13, No. 5, pp. 322-330 (2007).

* cited by examiner

*Primary Examiner* — Suzette J Gherbi
(74) *Attorney, Agent, or Firm* — Squire Patton Boggs (US) LLP

(57) ABSTRACT

This invention relates to the use of dual variable domain antibodies to locate naturally-occurring beneficial agents or therapeutic agents at a region of stent implantation in diabetic patients who have undergone stent implantation.

10 Claims, No Drawings

METHOD OF REDUCING MACE IN DIABETIC PATIENTS SUBSEQUENT TO STENT PLACEMENT

FIELD

The present invention relates to a method of treating a diabetic patient undergoing, or who has undergone, stent placement, the goal being to prevent or ameliorate the subsequent occurrence of major adverse cardiac events (MACE). The method comprises capturing and thereby lengthening the residence time of naturally-occurring beneficial agents, in the vicinity of stent placement.

BACKGROUND

Until the mid-1980s, the accepted treatment for coronary atherosclerosis, i.e., narrowing of the coronary artery(ies) was coronary by-pass surgery. While being quite effective and having evolved to a relatively high degree of safety for such an invasive procedure, by-pass surgery still involves potentially serious complications and generally results in an extended recovery period.

With the advent of percutaneous transluminal coronary angioplasty (PTCA) in 1977, the scene changed dramatically. Using catheter techniques originally developed for heart exploration, inflatable balloons were deployed to re-open occluded regions in arteries. The procedure was relatively non-invasive, took a short time compared to by-pass surgery and recovery time was minimal. However, PTCA brought with it its own problems including vasospasm, elastic recoil of the stretched arterial wall and restenosis, the re-clogging of the treated artery due to neointimal hyperplasia in the vicinity of the procedure, any of which could undo much of what was accomplished.

The next improvement, advanced in the mid-1980s, was the use of a stent to maintain a luminal diameter that had been re-established using PTCA. This for all intents and purposes put an end to vasospasm and elastic recoil but did not resolve the issue of restenosis. That is, prior to the introduction of stents, restenosis occurred in about 30 to 50% of patients undergoing PTCA. Stenting reduced this to about 15 to 20%, a substantial improvement but still more than desirable.

In 2003, the drug-eluting stent (DES) was introduced. The drugs initially used with DESs were cytostatic compounds, that is, compounds that curtailed the proliferation of cells that fostered restenosis. The occurrence of restenosis was reduced to about 5 to 7%, a relatively acceptable figure. However, the use of DESs engendered yet another complication, late stent thrombosis, the forming of blood clots some time after the stent was in place. It was hypothesized that the formation of blood clots was most likely due to delayed healing, a side-effect of the use of cytostatic drugs.

The physiopathology of restenosis involves early injury to smooth muscle cells (SMCs), de-endothelialization and thrombus deposition. Over time, this leads to SMC proliferation and migration and extra-cellular matrix deposition. There is an increasing body of evidence suggesting that inflammation plays a pivotal role in linking early vascular injury with neointimal growth and eventual lumen compromise, i.e., restenosis. Further, it has been observed that, when stents are used, the inflammatory state if often more intense and prolonged, exacerbating the situation.

Inflammation is, of course, a normal response to injury and is a necessary element of the healing process. Chronic inflammation, however, can be detrimental to healing in that the continuous recruitment of monocytes, lymphocytes and neutrophils leads to a constant generation of inflammatory cytokines along with reactive oxygen species and enzymes generated by inflammatory cells to remove foreign bodies or damaged tissue. Thus, anti-inflammatory drugs are often included in DESs to control chronic inflammation by reducing cytokine-driven neointimal growth. Long-term administration of anti-inflammatory drugs, however, can shut down the healing process completely.

While generally effective, current DESs have not completely served certain subsets of patients. For example, in the SIRIUS clinical trial, patients with diabetes were roughly twice as likely as non-diabetics to incur binary restenosis. Further, diabetic patients tend to generally be more prone, post PCTA and stent placement, to target lesion revascularization (TLR) and to major adverse cardiac events (MACE). It has been observed that increased MACE such as acute myocardial infarction (AMI), thrombosis and cardiac death in diabetics during approximately the first year post stent placement correlate well with target lesion revascularization (TLR). TLR, in turn, correlates well with the presence of restenosis in or near a target lesion.

What is needed is a method of treating vascular disease in diabetics that addresses the increased risk of MACE both simply by virtue of the presence of diabetes and that associated with TLR. This invention provides such a method.

SUMMARY

Thus, an aspect of this invention is a method of reducing the incidence of major adverse cardiovascular events (MACE) in diabetic patients subsequent to stent implantation to treat a vascular disease, comprising:

delivering to a region of stent implantation a dual variable domain (DVD) antibody, wherein:

a first variable domain of the DVD antibody recognizes and binds to an entity specific to the region of stent implantation; and a second variable domain of the DVD antibody captures a naturally-occurring beneficial agent or a therapeutic agent, or the DVD antibody comprises one or more biotin molecules that do not interfere with the binding function of either of the variable arms of the DVD antibody;

the outermost surface of the stent comprises avidin or streptavidin such that when the DVD antibody encounters the outermost surface of the stent, the DVD antibody becomes bound to the outermost surface of the stent; and the first and second variable domains independently capture a naturally-occurring beneficial agent, a therapeutic agent or one variable domain captures a naturally-occurring beneficial agent and the other variable domain captures a therapeutic agent.

In an aspect of this invention, delivering the DVD antibody to the treatment site comprises streptavidin/biotin binding of the DVD antibody to the stent prior to implantation.

In an aspect of this invention delivering the DVD antibody to the treatment site comprises local delivery.

In an aspect of this invention, delivering the DVD antibody to the treatment region comprises systemic delivery of the DVD antibody.

In an aspect of this invention, the site that is recognized by the first variable domain of the DVD antibody comprises an exposed basement membrane protein.

In an aspect of this invention, the site that that is recognized by the first variable domain of the DVD antibody comprises a site of coagulation/thrombosis.

In an aspect of this invention, the beneficial agent that is recognized and bound by the second variable domain of the DVD antibody comprises an endothelial progenitor cell.

In an aspect of this invention, the therapeutic agent is cilostazol.

In an aspect of this invention, the therapeutic agent is a nitric oxide donor.

In an aspect of this invention, the vascular disease is a cardiovascular disease.

In an aspect of this invention, the vascular disease is a peripheral arterial disease (PAD).

An aspect of this invention is an implantable medical device to which is adhered a DVD antibody by biotin:avidin or biotin:streptavidin binding.

In an aspect of this invention, the implantable medical device comprises a stent.

DETAILED DESCRIPTION

It is understood that use of the singular throughout this application including the claims includes the plural and vice versa unless expressly stated otherwise. That is, "a" and "the" are to be construed as referring to one or more of whatever the word modifies. Non-limiting examples are: "an exposed basement membrane protein," which is understood to include one or more such proteins, and "a therapeutic agent," which is understood to include one or more such agents, unless it is expressly stated or is unambiguously obvious from the context that such is not intended.

As used herein, words of approximation such as, without limitation, "about," "substantially," "essentially" and "approximately" mean that the word or phrase modified by the term need not be exactly that which is written but may vary from that written description to some extent. The extent to which the description may vary will depend on how great a change can be instituted and have one of ordinary skill in the art recognize the modified version as still having the properties, characteristics and capabilities of the modified word or phrase. In general, but subject to the preceding discussion, a numerical value herein that is modified by a word of approximation may vary from the stated value by about ±15%.

As used herein, the use of "preferred," "preferably," or "more preferred," and the like refer to preferences as they existed at the time of filing of the patent application.

As used herein, "optional" means that the element modified by the term may, but is not required to, be present.

As used herein, "drug," "therapeutic agent" and "agent" are interchangeable and refer to a pharmaceutical substance used to treat a disease or disorder.

It is generally known that diabetics can present with more complex coronary lesions that tend to be more challenging to treat due to intrinsic diabetic complications. Treatment of vascular lesions directed specifically to diabetics, however, has been slow in developing even though the restenosis rate in diabetics is currently in double digits, especially for longer lesions, while for non-diabetic patients the restenosis rate can be as low as 1.8%. It is currently estimated by the Center for Disease Control and Prevention (CDC) that one in ten Americans has diabetes in some form. The prediction for the future is not encouraging in that the CDC predicts that, by the year 2050, one in three Americans will have diabetes. While efforts are being made to lower these numbers by lifestyle and dietary changes, most likely such efforts will have a limited impact. Due to the large fraction of the general populace already afflicted with diabetes and the prediction of an even higher proportion in the future, treatments directed toward diabetics is much needed.

Target lesion revascularization (TLR) refers to a re-intervention, e.g., by percutaneous revascularization or surgical bypass, performed for ≥50% diameter stenosis, which is confirmed by angiography, within ±5 mm proximal to, distal to, or both proximal and distal to, a target lesion after documentation of recurrent clinical symptoms of peripheral arterial disease following the initial procedure. The clinical symptoms can include, without limitation, ischemic symptoms or a positive functional ischemia study. Diabetes has been found to be a strong predictor of short-term restenosis. It is the intent of this invention to reduce occurrence of short-term restenosis, concomitantly reduce the need for TLR and, by doing so, reduce substantially the risk of MACE in diabetic patients, whether such MACE is related to the TLR or not.

As used herein, an "implantable medical device" refers to any type of appliance that is totally or partly introduced, surgically or medically, into a patient's body or by medical intervention into a natural orifice, and which is intended to remain there after the procedure. The duration of implantation may be essentially permanent, i.e., intended to remain in place for the remaining lifespan of the patient; until the device biodegrades; or until it is physically removed. Examples of implantable medical devices include, without limitation, implantable cardiac pacemakers and defibrillators; leads and electrodes for the preceding; implantable organ stimulators such as nerve, bladder, sphincter and diaphragm stimulators, and cochlear implants; prostheses, vascular grafts, self-expandable stents, balloon-expandable stents, stent-grafts, grafts, artificial heart valves, patent foramen ovale closure devices, left atrial appendage excluders, and cerebrospinal fluid shunts.

Presently preferred implantable medical devices of this invention are stents. A stent refers generally to any device used to hold tissue in place in a patient's body. Very often, stents are employed for the localized delivery of therapeutic agents to one or more specific treatment sites in a patient's body. Particularly useful stents are those used for the maintenance of the patency of a vessel in a patient's body when the vessel is narrowed or closed due to diseases or disorders including, without limitation, tumors (in, for example, bile ducts, the esophagus, the trachea/bronchi, etc.), benign pancreatic disease, coronary artery disease, carotid artery disease and peripheral arterial disease such as atherosclerosis, restenosis and vulnerable plaque. Vulnerable plaque (VP) refers to a fatty build-up in an artery thought to be caused by inflammation. The VP is covered by a thin fibrous cap that can rupture leading to blood clot formation. A stent can be used to strengthen the wall of the vessel in the vicinity of the VP and act as a shield against such rupture. A stent can be used in, without limitation, neuro, carotid, coronary, pulmonary, aorta, renal, biliary, iliac, femoral and popliteal as well as other peripheral vasculatures. A stent can be used in the treatment or prevention of disorders such as, without limitation, thrombosis, restenosis, hemorrhage, vascular dissection or perforation, vascular aneurysm, chronic total occlusion, claudication, anastomotic proliferation, bile duct obstruction and ureter obstruction.

A stent used for patency maintenance is usually delivered to the target site in a compressed state and then expanded to fit the vessel into which it has been inserted. Once at a target location, a stent may be self-expandable or balloon expandable.

By "outermost surface" of a stent is meant any surface of the stent, however spatially oriented, that would be in contact with bodily tissue or fluids when the device is fully deployed in a patient.

As used herein, "systemic delivery" refers to the administration of a DVD antibody agent or a therapeutic agent into a patient's body at a location that is generally remote from the target site undergoing treatment. The DVD antibody then circulates more or less randomly throughout the body until at least a portion of the administered drug eventually finds its way to the target locale.

As used herein, "local delivery" refers to the administration of a DVD antibody or a therapeutic agent directly to the site of stent implantation. Such direct administration may be by, without limitation, percutaneous injection or delivery through a catheter, which catheter may be the same device used to implant the stent.

As used herein, an "antibody" has its normal meaning, as understood by those of ordinary skilled in the art. Briefly, an antibody is a Y-shaped immunoglobin (Ig) molecule comprised of four polypeptide chains, two heavy chains and two light chains. The heavy and light chains each have constant domains at one end, the constant end of the heavy chain forming the base of the "Y" and variable domains at their tips, which variable domains together form the arms of the "Y". Each variable domain terminates in what is known as a hypervariable region, which is the portion of the antibody responsible for binding to foreign objects encountered in the body. Generally both arms of the antibody Y comprise the same hypervariable region such that a given antibody generally binds to one and only one foreign object.

A "dual variable domain antibody" or "DVD antibody" on the other hand, refers to a synthetic antibody in which the hypervariable regions on a single antibody can be engineered to be different and thereby individually capable of binding to different foreign bodies. Such DVD antibodies and methods of preparing them are fully set forth in U.S. patent application Ser. No. 12/459,624, which is incorporated herein in its entirety as if fully set forth, including any figures.

As used herein, "recognizes and binds," as applied to an antibody simply connotes the process by which a hypervariable domain of an antibody that been engineered to attach itself to a specific foreign body interacts with the foreign body. That is, when an antibody encounters a foreign body that that antibody is predisposed by its nature or by its engineered properties to interact with, the hypervariable region of the antibody "recognizes" the foreign body in a lock-and-key fashion. Once so recognized, the foreign body is reversibly or irreversibly bound by chemical or physical forces.

As used herein, "capture" refers to the process whereby a DVD that is itself restricted to a treatment site recognizes and binds to a circulating naturally-occurring beneficial agent and thereby localizes that agent at the treatment site. It is understood that the capture of the circulating agent should not negatively affect the beneficial property(ies) of the agent.

In an embodiment of this invention, one of the arms of the "Y" of a DVD antibody, referred to herein as a "first variable domain" is engineered to function as a treatment site targeting entity. That is, the first variable domain comprises a hypervariable region that is engineered to recognize and bind to a foreign body that is exclusive to, or at least substantially exclusive to, the treatment site and thereby localize the antibody at the treatment site.

With regard to stented vessels, such a foreign body exclusive to the site of stent implantation may be an exposed basement membrane protein. A basement membrane refers to a thin layer of connective tissue that underlies the epithelium that lines cavities and surfaces of organs or, of more import with regard to the present invention, underlies the endothelium, which lines the vessels of the vascular system. When the endothelium is breached, as is normally the situation during stenting, the basement membrane may become exposed. The basement membrane comprises proteins such as, without limitation, tissue-specific isoforms of collagen IV, laminin-entactin/nidogen complexes comprising equally tissue-specific isoforms of laminin and particular populations of proteoglucans not elsewhere found. A DVD antibody, as is the wont of all antibodies, can be exquisitely tailored to recognize and bind solely to these proteins thereby permitting the systemic administration of a DVD antibody, secure in the knowledge that the antibody will eventually reach the treatment, i.e., stented, site and will be retained there by virtue of recognizing and binding to one of the basement membrane proteins.

Other foreign bodies that may be considered to be exclusive to a site of stent implantation (assuming the patient has not suffered a traumatic injury to some other portion of the body) comprise proteins associated with coagulation/thrombosis such as, without limitation, coagulation factors, which are generally serine proteases (although there are exceptions well-known to those skilled in the art), platelet membrane proteins, generally specific glycoproteins, and fibrin. A DVD antibody may be engineered to recognize and bind to any of these proteins.

It is understood that the biochemical composition at the site of stent implantation is extremely complex and that the above exemplary foreign bodies that are specific to such site and that can be recognized and bound by DVD antibodies are not intended, nor are they to be construed, to limit the scope of this invention in any manner. Based on the teachings herein, the skilled artisan will be able to ascertain other site-specific proteins to which DVD antibodies may be engineered to recognize and bind. All such biological binding sites are within the scope of this invention.

A mechanical method of localizing a DVD antibody to a site of stent placement is simply to adhere the DVD antibody to the exterior surface of a stent. While this can be accomplished by including peptide chains on the outermost surface of the stent and contacting the surface with a DVD antibody engineered such that the first variable domain recognizes and binds to that peptide, it is presently preferred to keep both variable domains of the DVD antibody free to bind to other foreign bodies. To accomplish this, a DVD antibody of this invention may be adhered to the exterior surface of a stent by biotinylating the DVD antibody and including avadin or streptavidin on the outermost surface of the stent or vice versa, i.e., biotinylating the outermost surface of the stent and adhering avadin or streptavidin to the antibody. The well-known natural binding affinity of avadin and streptavidin for biotin will result in the DVD antibody adhering to the stent when the antibody comes in contact with the stent surface.

The first variable domain of a DVD antibody of this invention may be used to localize the antibody at a treatment site while the second variable domain may be used to capture a beneficial agent at the treatment site and thereby assure its long-term presence at the site.

As used herein a "naturally-occurring beneficial agent" or simply a "beneficial agent," the two being used interchangeable herein, refers to a substance or physical entity that is an integral part of the biochemistry of an animal. While the animal may be of any species, of primary interest at present are mammalian species such as domestic animals and, in particular, human beings. The substance or physical entity may be present at all times in the animal or it may arise or be biosynthesized in response to a challenge to the animal's internal well-being. For the purposes of this invention such challenges may take the form of, without limitation, excessive inflammation, accumulation of macrophage and thrombosis.

A specific but non-limiting example of a naturally-occurring beneficial agent that could be captured by one of the variable arms of a DVD antibody and thence localized at the site of stent implantation could be a beneficial cell type such as, without limitation, endothelial progenitor cells. Endothelial progenitor cells function to restore the lining of damaged blood vessels. Endothelial progenitor cells are usually found in the circulating blood stream. Evidence suggests that high levels of circulating endothelial progenitor cells leads to better outcomes and fewer repeat heart attacks in patients. Since heart attacks constitute a MACE, it is postulated that localization of endothelial progenitor at the site of stent implantation could provide a substantial enhancement in the repair of damage to the endothelium resulting from stenting and concurrent reduce MACE.

As used herein, "long-term presence" of a beneficial agent means that the normally circulating agent is engaged and held at the treatment site until it has had the opportunity to perform its beneficial function as opposed to having only chance encounters with it specific target as the agent systemically circulates through the subject's body. It is understood that the exact meaning of "long-term" is dependent on the pharmacodynamics of the beneficial agent, and such will, of course, vary with the nature of the agent. For the purposes of this invention, "long-term" refers to any time-span over which the beneficial agent is capable of performing its beneficial function.

As used herein, "therapeutic agent" or "drug" refers to an extrinsic substance that, when administered in a therapeutically effective amount to a patient suffering from a disease, has a therapeutic beneficial effect on the health and well-being of the patient. A therapeutic beneficial effect on the health and well-being of a patient includes, but it not limited to: (1) curing the disease; (2) slowing the progress of the disease; (3) causing the disease to retrogress; or, (4) alleviating one or more symptoms of the disease. As used herein, a therapeutic agent also includes any substance that when administered to a patient, known or suspected of being particularly susceptible to a disease, in a prophylactically effective amount, has a prophylactic beneficial effect on the health and well-being of the patient. A prophylactic beneficial effect on the health and well-being of a patient includes, but is not limited to: (1) preventing or delaying on-set of the disease in the first place; (2) maintaining a disease at a retrogressed level once such level has been achieved by a therapeutically effective amount of a substance, which may be the same as or different from the substance used in a prophylactically effective amount; or, (3) preventing or delaying recurrence of the disease after a course of treatment with a therapeutically effective amount of a substance, which may be the same as or different from the substance used in a prophylactically effective amount, has concluded.

As used herein, "treating" refers to the administration of a therapeutically effective amount of a therapeutic agent to a patient known or suspected to be afflicted with a vascular disease.

A "therapeutically effective amount" refers to that amount of a therapeutic agent that will have a beneficial effect, which may be curative or palliative, on the health and well-being of the patient with regard to the vascular disease with which the patient is known or suspected to be afflicted.

As used herein, a "diabetic patient" refers primarily to a human being that presents with diagnosed type 1 or type 2 diabetes mellitus. In addition, however, for the purposes of this invention a "diabetic patient" also refers to one who, while not necessarily exhibiting all the characteristic of full-blown diabetes, presents with a compromised vasculature that exhibits the negative characteristics, such as chronic inflammation, associated with a patient suffering from diagnosed type 1 or type 2 diabetes.

As used herein, a "treatment region" refers to the site of actual stent placement as well as regions proximal and distal to that site. The regions proximal and distal to the site of implantation may vary in length but would typically be considered to be about 5 to 10 mm from the ends of the stent.

As used herein, a "vascular disease" refers to a disease of the vessels, primarily arteries and veins, which transport blood to and from the heart, brain and peripheral organs such as, without limitation, the arms, legs, kidneys and liver. In particular "vascular disease" refers to the coronary arterial and venous systems, the carotid arterial and venous systems, the aortic arterial and venous systems and the peripheral arterial and venous systems. The disease may be, without limitation, atherosclerosis, vulnerable plaque, restenosis or peripheral arterial disease. Peripheral vascular disease includes arterial and venous diseases of the renal, iliac, femoral, popliteal, tibial and other vascular regions.

Peripheral vascular diseases are generally related to structural changes in blood vessels caused by such conditions as inflammation and tissue damage. A subset of peripheral vascular disease is peripheral artery disease (PAD). PAD is a condition that is similar to carotid and coronary artery disease in that it is caused by the buildup of fatty deposits on the lining or intima of the artery walls. Just as blockage of the carotid artery restricts blood flow to the brain and blockage of the coronary artery restricts blood flow to the heart, blockage of the peripheral arteries can lead to restricted blood flow to the kidneys, stomach, arms, legs and feet. In particular at present a peripheral vascular disease refers to a disease of the superficial femoral artery.

In addition to naturally-occurring beneficial entities, extrinsic therapeutic agents may also be captured at, if administration is systemic, a treatment site by a DVD antibody by means of one of the other of the variable domains of the antibody, which domain has been engineered to recognize and bind to the particular agent. A broad spectrum of agents may be so administered. For example, suitable therapeutic agents include, without limitation, antiproliferative agents, anti-inflammatory agents, antineoplastics, antimitotics, anti-platelets, anticoagulants, antifibrins, and antithrombins, cytostatic agents, antibiotics, antiallergic agents and antioxidants.

While representative therapeutic agents from any of the above families of agents may be used in the method of this invention, it is presently preferred that a combination of an antiproliferative agent and an anti-inflammatory agent be delivered to the site of stent implantation, usually as components of a DES.

In general, suitable antiproliferative agents include, without limitation, actinomycin D, or derivatives or analogs thereof, i.e., actinomycin D is also known as dactinomycin, actinomycin IV, actinomycin $I_1$, actinomycin $X_1$, and actinomycin Antiproliferative agents can be natural proteineous agents such as a cytotoxin or a synthetic molecule, all taxoids such as taxols, docetaxel, and paclitaxel, paclitaxel derivatives, all rapamycin-derived drugs such as macrolide antibiotics, rapamycin, everolimus, structural derivatives and functional analogues of rapamycin, structural derivatives and functional analogues of everolimus, FKBP-12 mediated mTOR inhibitors, biolimus, perfenidone, prodrugs thereof, co-drugs thereof, and combinations thereof. Representative rapamycin derivatives and analogs include 40-O-(2-hydroxyethyl)rapamycin (EVEROLIMUS®), 40-O-(3-hydroxypropyl)rapamycin, 40-O-[2-(2-hydroxy)ethoxy]ethyl-rapamycin, 40-O-tetrazolylrapamycin, or 40-epi-(N1-tetrazolyl)-rapamycin, prodrugs thereof, co-drugs thereof, and combinations thereof.

Presently preferred antiproliferative agents for use in DESs are the mTOR inhibitors, which include, without limitation, everolimus, zotarolimus, sirolimus, biolimus, myolimus, novolimus, temsirolimus, deforolimus and combinations thereof, with everolimus being particularly preferred. Everolimus is a semi-synthetic derivative of rapamycin, a naturally product isolated from *Streptomyces hydroscopicus*, and is prepared by substituting a 2-hydroxyethoxy moiety for the hydroxyl group at position 42 of rapamycin. Everolimus is quite hydrophobic, which is an advantageous property with regard to delivery of the compound from a drug reservoir layer of a stent. That is, the compound's hydrophobicity permits slow sustained release from a hydrophobic polymer, which in turn facilitates maintenance of therapeutic drug levels eluting from the drug reservoir layer of the stent. Very low water solubility also leads to a long residence time in tissues. Further, its lipophilic character favors crossing of cell membranes to inhibit neointimal proliferation of target tissues.

While being very effective in the prevention of restenosis generally, everolimus has properties that, while not detracting to a clinically significant degree from its value as a therapeutic agent for treatment of vascular diseases in patients otherwise healthy, may be quite detrimental to the overall well-being of diabetic patients. That is, everolimus (and for that matter, essentially all the derivatives of sirolimus (rapamycin) and sirolimus itself as well) has been shown to elevate PAI-1 in patients, which can lead to increased risk of coagulation/thrombosis, decreased eNOS, which can result in increased smooth muscle cell proliferation and increased SIRT1, which may lead to endothelial cell senescence. While these properties are not necessarily inconsequential even to non-diabetic patients, the beneficial properties of everolimus over-shadow the potential negative aspects in non-diabetics. With diabetics, however, it is postulated that these negative side effects may, if not cause, at least facilitate MACE. It is therefore an embodiment of this invention that the drug cilostazol be substituted for, or at least for a portion of, the above mTOR inhibitors in diabetic patients.

It is believed that cilostazol would benefit diabetic patients undergoing DES implantation because cilostazol is known to (1) directly inhibit platelets; (2) inhibit restenosis, for which diabetes is a strong predictor; (3) elevate eNOS, which should promote vasodilation and inhibit thrombosis and smooth muscle cell proliferation; and (4) activate SIRT1, which would have the effect of reversing endothelial cell senescence induced by the rapamycin mTOR inhibitors.

Suitable anti-inflammatory agents that can be used in combination with the mTOR inhibitor and cilostazol of this invention include, without limitation, cilostazol, clobetasol, alclofenac, alclometasone dipropionate, algestone acetonide, alpha amylase, amcinafal, amcinafide, amfenac sodium, amiprilose hydrochloride, anakinra, anirolac, anitrazafen, apazone, balsalazide disodium, bendazac, benoxaprofen, benzydamine hydrochloride, bromelains, broperamole, budesonide, carprofen, ciclofrofen, cintazone, cliprofen, clobetasol propionate, clobetasone butyrate, clopirac, cloticasone propionate, cormethasone acetate, cortodoxone, deflazacort, desonide, desoximetasone, dexamethasone dipropionate, diclofenac potassium, diclofenac sodium, diflorasone diacetate, diflumidone sodium, diflunisal, difluprednate, diftalone, dimethyl sulfoxide, drocinonide, endrysone, enlimomab, enolicam sodium, epirizole, etodolac, etofenamate, felbinac, fenamole, fenbufen, fenclofenac, fenclorac, fendosal, fenpipalone, fentiazac, flazalone, fluazacort, flufenamic acid, flumizole, flunisolide acetate, flunixin, flunixin meglumine, fluocortin butyl, fluorometholone acetate, fluquazone, flurbiprofen, fluretofen, fluticasone propionate, furaprofen, furobufen, halcinonide, halobetasol propionate, halopredone acetate, ibufenac, ibuprofen, ibuprofen aluminum, ibuprofen piconol, ilonidap, indomethacin, indomethacin sodium, indoprofen, indoxole, intrazole, isoflupredone acetate, isoxepac, isoxicam, ketoprofen, lofemizole hydrochloride, lomoxicam, loteprednol etabonate, meclofenamate sodium, meclofenamic acid, meclorisone dibutyrate, mefenamic acid, mesalamine, meseclazone, methylprednisolone suleptanate, momiflumate, nabumetone, naproxen, naproxen sodium, naproxol, nimazone, olsalazine sodium, orgotein, orpanoxin, oxaprozin, oxyphenbutazone, paranyline hydrochloride, pentosan polysulfate sodium, phenbutazone sodium glycerate, pirfenidone, piroxicam, piroxicam cinnamate, piroxicam olamine, pirprofen, prednazate, prifelone, prodolic acid, proquazone, proxazole, proxazole citrate, rimexolone, romazarit, salcolex, salnacedin, salsalate, sanguinarium chloride, seclazone, sermetacin, sudoxicam, sulindac, suprofen, talmetacin, talniflumate, talosalate, tebufelone, tenidap, tenidap sodium, tenoxicam, tesicam, tesimide, tetrydamine, tiopinac, tixocortol pivalate, tolmetin, tolmetin sodium, triclonide, triflumidate, zidometacin, zomepirac sodium, aspirin (acetylsalicylic acid), salicylic acid, corticosteroids, glucocorticoids, tacrolimus, pimecorlimus and prodrugs, co-drugs and combinations thereof.

Presently preferred anti-inflammatory agents for use in the present invention are dexamethasone and clobetasol. Derivatives of dexamethasone such as, without limitation, dexamethasone acetate, dexamethasone laurate, dexamethasone-tert-butylacetate, dexamethasone tetrahydrophthalate, and dexamethasone isonicotinate might also be used.

Another family of therapeutic agents that could be localized at a site of stent implantation using a DVD antibody would be nitric oxide, NO, donor compounds. While chronic expression of NO has been associated Type 1 diabetes, NO tends to not be produced by endothelial cells of diabetics, exactly where and when it is needed to assist in promoting endothelial cell migration and proliferation and thereby healing of a stented treatment site. NO donors include, without limitation, nitroglycerin, S-nitrosothiols, diazeniumdiolate, also known as NONOates, furoxan and nitroaspirin, "Thrombosis" refers to the formation or presence of a blood clot (thrombus) inside a blood vessel or chamber of the heart. A blood clot that breaks off and travels to another part of the body is called an embolus. If a clot blocks a blood vessel that feeds the heart, it causes a heart attack. If a clot blocks a blood vessel that feeds to brain, it causes a stroke. The precursor to a thrombosis is coagulation, which refers to the cascade process beginning with the exposure of the blood in a vessel to proteins such as tissue factor, which initiate changes in blood platelets and the plasma protein, fibrogen. In response to these changes, proteins in the blood plasma, referred to as coagulation or clotting factors, work together in a complex cascade to form fibrin strands, which act to cover and protect the injured tissue and prevent further blood loss. This is, of course, a normal, desired occurrence in healthy individuals but it may become pathological in compromised individuals such as those undergoing surgery, older patients and diabetics. In these instances the coagulation can ultimately result in thrombosis, defined as the pathological formation of blood clots. Thrombosis may in turn result in clot release, which is termed an embolus. The embolus can then migrate to other parts of the body with concurrent interference with blood circulation and subsequent impairment of organ function downstream of the embolus. MACE readily result from coagulation/thrombosis, which is therefore preferentially avoided or at the very least substantially ameliorated, an embodiment of this invention. Naturally occurring endogenous substances that could be captured at a site of stent implantation includes, without limitation, fibrinolytics (tissue plasminogen activator (tPA), urokinase, plasmin and plasminogen. In addition, drugs that could be systematically administered and similarly captured at a site of stent implantation include, again without limitation, anticoagulants such as, but not limited, to heparin, warfarin and coumadin and thrombin inhibitors such as, but not limited to, hirudin, bivalirudin and argatroban).

With regard to including the DVD antibody on an outermost surface of a DES, the outermost surface may comprise a drug reservoir layer, a drug release rate controlling layer or simply a protective layer. The fabrication of DESs with the foregoing layers is very well-known in the art and need not be described in detail herein. In brief, however, it is noted that a DES is generally comprised of: (1) a primer layer, which is optional, and that consists of a polymer or blend of polymers that exhibit good adhesion characteristics with regard to the material of which the device body is manufactured and good adhesion characteristics with regard to whatever material is to be coated on the device body. Thus, a primer layer serves as an intermediary layer between a device body and materials to be affixed to the device body and is, therefore, applied directly to the device body. Examples of primers, without limitation, include acrylate and methacrylate polymers with poly(n-butyl methacrylate) (PBMA) being a presently preferred primer; (2) a "drug reservoir layer," which refers either to a layer of one or more therapeutic agents applied neat or as a layer of polymer or blend of polymers that has dispersed within its three-dimensional structure one or more therapeutic agents. A polymeric drug reservoir layer is designed such that, by one mechanism or another, e.g., without limitation, by elution or as the result of biodegradation of the polymer, the therapeutic substance is released from the layer into the surrounding environment. The drug reservoir layer may constitute the outermost layer of the DES; and (3) optionally, a separate rate-controlling layer, which refers to a polymer layer that controls the release of therapeutic agents or drugs into the environment. Other layers and multiples of layers may also be included on a DES. As mentioned above, these aspects of DESs are well-known in the art and the method of this invention encompasses any and all manner of DES.

What is claimed:

1. A method of reducing the incidence of major adverse cardiovascular events (MACE) in diabetic patients subsequent to stent implantation to treat a vascular disease, comprising:
    delivering to a region of stent implantation a dual variable domain (DVD) antibody, wherein:
        a first variable domain of the DVD antibody recognizes and binds to an exposed basement membrane protein underlying an endothelium, or a site of coagulation/thrombosis, at the region of stent implantation; and
        a second variable domain of the DVD antibody captures a naturally-occurring beneficial agent or a therapeutic agent.

2. The method of claim 1, wherein delivering the DVD antibody to the treatment site comprises local delivery.

3. The method of claim 1, wherein delivering the DVD antibody to the treatment region comprises systemic delivery of the DVD antibody.

4. The method of claim 1, wherein the beneficial agent that is recognized and bound by the second variable domain of the DVD antibody comprises an endothelial progenitor cell.

5. The method of claim 1, wherein the therapeutic agent is cilostazol.

6. The method of claim 1, wherein the therapeutic agent is a nitric oxide donor.

7. The method of claim 1, wherein the vascular disease is a cardiovascular disease.

8. The method of claim 1, wherein the vascular disease is a peripheral arterial disease (PAD).

9. The method of claim 1, wherein the basement membrane protein is selected from collagen IV, laminin, and entactin.

10. The method of claim 1, wherein the DVD antibody recognizes and binds to a protein selected from a serine protease, a platelet membrane protein, and fibrin.

* * * * *